US010413349B2

United States Patent
(12) United States Patent
Chernov et al.

(10) Patent No.: US 10,413,349 B2
(45) Date of Patent: Sep. 17, 2019

(54) SYSTEM AND METHODS FOR IDENTIFYING TISSUE AND VESSELS

(75) Inventors: Boris Chernov, Saint-Petersburg (RU); Nataliya Chernova, legal representative, Saint-Petersburg (RU); Igoris Misuchenko, Saint-Petersburg (RU); Georgy Martsinovskiy, Saint-Petersburg (RU); Mikhail Verbitsky, Stoughton, MA (US)

(73) Assignee: COVIDIEN LP, Mansfield, MA (US)

( * ) Notice: Subject to any disclaimer, the term of this patent is extended or adjusted under 35 U.S.C. 154(b) by 685 days.

(21) Appl. No.: 13/040,347

(22) Filed: Mar. 4, 2011
(Under 37 CFR 1.47)

(65) Prior Publication Data

US 2012/0226272 A1 Sep. 6, 2012

(51) Int. Cl.
*A61B 17/00* (2006.01)
*A61B 18/00* (2006.01)
(Continued)

(52) U.S. Cl.
CPC ........ *A61B 18/1442* (2013.01); *A61B 5/0295* (2013.01); *A61B 5/053* (2013.01);
(Continued)

(58) Field of Classification Search
CPC . A61B 8/06; A61B 5/053; A61B 2018/00875; A61B 18/1445;
(Continued)

(56) References Cited

U.S. PATENT DOCUMENTS

| | | | |
|---|---|---|---|
| D249,549 | S | 9/1978 | Pike |
| D263,020 | S | 2/1982 | Rau, III |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.
(Continued)

*Primary Examiner* — Christian Jang
*Assistant Examiner* — Karen E Toth

(57) ABSTRACT

A surgical system and corresponding methods for identifying tissue or vessels and assessing their conditions includes a probing signal source for applying a probing signal to the tissue and a response signal monitor for monitoring a response signal that varies according to the level of blood circulation in the tissue or vessels. The response signal monitor monitors the response signal over an interval equal to or longer than an interval between two successive cardiac contractions. The surgical system includes a microprocessor that analyzes the amplitude and/or phase of the response signal to determine the level of blood circulation in the tissue or in different portions of the tissue, and determines a tissue parameter based upon the level of blood circulation. The surgical system may monitor a cardiac signal related to cardiac contractions and correlate the response signal and the cardiac signal to determine a level of blood circulation in the tissue.

13 Claims, 5 Drawing Sheets

(51) Int. Cl.
*A61B 18/14* (2006.01)
*A61B 5/053* (2006.01)
*A61B 5/0295* (2006.01)

(52) U.S. Cl.
CPC ............... *A61B 2017/00106* (2013.01); *A61B 2018/0063* (2013.01); *A61B 2018/00636* (2013.01); *A61B 2018/00642* (2013.01); *A61B 2018/00648* (2013.01); *A61B 2018/00875* (2013.01); *A61B 2018/00982* (2013.01)

(58) Field of Classification Search
CPC ........... A61B 2017/00022; A61B 2017/00026; A61B 2018/00404; A61B 2018/0063; A61B 2018/00702; A61B 18/18; A61B 2018/00642; A61B 2018/00648
USPC .................................................. 600/300, 481
See application file for complete search history.

(56) References Cited

U.S. PATENT DOCUMENTS

| | | | | |
|---|---|---|---|---|
| 4,597,393 | A * | 7/1986 | Yamakoshi et al. | 600/490 |
| D295,893 | S | 5/1988 | Sharkany et al. | |
| D295,894 | S | 5/1988 | Sharkany et al. | |
| D298,353 | S | 11/1988 | Manno | |
| D299,413 | S | 1/1989 | Decarolis | |
| D343,453 | S | 1/1994 | Noda | |
| D348,930 | S | 7/1994 | Olson | |
| D349,341 | S | 8/1994 | Lichtman et al. | |
| D354,564 | S | 1/1995 | Medema | |
| D358,887 | S | 5/1995 | Feinberg | |
| D384,413 | S | 9/1997 | Zlock et al. | |
| H1745 | H | 8/1998 | Paraschac | |
| 5,810,010 | A * | 9/1998 | Anbar | 600/474 |
| 5,810,762 | A * | 9/1998 | Hofmann | A61N 1/327 604/20 |
| D402,028 | S | 12/1998 | Grimm et al. | |
| D408,018 | S | 4/1999 | McNaughton | |
| D416,089 | S | 11/1999 | Barton et al. | |
| 6,002,958 | A * | 12/1999 | Godik | 600/407 |
| D424,694 | S | 5/2000 | Tetzlaff et al. | |
| D425,201 | S | 5/2000 | Tetzlaff et al. | |
| H1904 | H | 10/2000 | Yates et al. | |
| D449,886 | S | 10/2001 | Tetzlaff et al. | |
| D453,923 | S | 2/2002 | Olson | |
| D454,951 | S | 3/2002 | Bon | |
| D457,958 | S | 5/2002 | Dycus et al. | |
| D457,959 | S | 5/2002 | Tetzlaff et al. | |
| 6,385,474 | B1 * | 5/2002 | Rather et al. | 600/407 |
| H2037 | H | 7/2002 | Yates et al. | |
| D465,281 | S | 11/2002 | Lang | |
| D466,209 | S | 11/2002 | Bon | |
| D493,888 | S | 8/2004 | Reschke | |
| 6,776,760 | B2 * | 8/2004 | Marmarelis | 600/448 |
| D496,997 | S | 10/2004 | Dycus et al. | |
| D499,181 | S | 11/2004 | Dycus et al. | |
| D502,994 | S | 3/2005 | Blake, III | |
| D509,297 | S | 9/2005 | Wells | |
| D525,361 | S | 7/2006 | Hushka | |
| D531,311 | S | 10/2006 | Guerra et al. | |
| D533,274 | S | 12/2006 | Visconti et al. | |
| D533,942 | S | 12/2006 | Kerr et al. | |
| D535,027 | S | 1/2007 | James et al. | |
| D538,932 | S | 3/2007 | Malik | |
| D541,418 | S | 4/2007 | Schechter et al. | |
| D541,611 | S | 5/2007 | Aglassinger | |
| D541,938 | S | 5/2007 | Kerr et al. | |
| 7,217,266 | B2 | 5/2007 | Anderson et al. | |
| D545,432 | S | 6/2007 | Watanabe | |
| D547,154 | S | 7/2007 | Lee | |
| D564,662 | S | 3/2008 | Moses et al. | |
| D567,943 | S | 4/2008 | Moses et al. | |
| D575,395 | S | 8/2008 | Hushka | |
| D575,401 | S | 8/2008 | Hixson et al. | |
| D582,038 | S | 12/2008 | Swoyer et al. | |
| D617,900 | S | 6/2010 | Kingsley et al. | |
| D617,901 | S | 6/2010 | Unger et al. | |
| D617,902 | S | 6/2010 | Twomey et al. | |
| D617,903 | S | 6/2010 | Unger et al. | |
| D618,798 | S | 6/2010 | Olson et al. | |
| D621,503 | S | 8/2010 | Otten et al. | |
| D627,462 | S | 11/2010 | Kingsley | |
| D628,289 | S | 11/2010 | Romero | |
| D628,290 | S | 11/2010 | Romero | |
| D630,324 | S | 1/2011 | Reschke | |
| 2003/0004432 | A1 * | 1/2003 | Assenheimer | 600/547 |
| 2003/0138378 | A1 * | 7/2003 | Hashimshony | 424/9.6 |
| 2004/0015163 | A1 * | 1/2004 | Buysse | A61B 18/1206 606/34 |
| 2007/0016050 | A1 * | 1/2007 | Moehring et al. | 600/454 |
| 2007/0038209 | A1 | 2/2007 | Buysse et al. | |
| 2008/0188736 | A1 | 8/2008 | Bambot et al. | |
| 2008/0255457 | A1 * | 10/2008 | Khoobehi et al. | 600/476 |
| 2008/0287815 | A1 * | 11/2008 | Chon et al. | 600/507 |
| 2009/0043217 | A1 * | 2/2009 | Hui | A61B 5/0002 600/509 |
| 2009/0204114 | A1 * | 8/2009 | Odom | A61B 18/1206 606/51 |
| 2010/0016810 | A1 * | 1/2010 | Drews et al. | 604/272 |
| 2010/0036379 | A1 * | 2/2010 | Prakash et al. | 606/51 |
| 2010/0160791 | A1 | 6/2010 | Liu et al. | |
| 2012/0059245 | A1 * | 3/2012 | Buschmann et al. | 600/419 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |

(56) References Cited

FOREIGN PATENT DOCUMENTS

| | | |
|---|---|---|
| JP | 2001-190564 | 7/2001 |
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 05/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,970, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

(56) References Cited

OTHER PUBLICATIONS

Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.

(56) References Cited

OTHER PUBLICATIONS

Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 12157891.8 dated Jun. 13, 2012.
European Office Action dated Oct. 11, 2017 in corresponding European Patent Application No. 12157891.8, 4 pages.

* cited by examiner

SYSTEM AND METHODS FOR IDENTIFYING TISSUE AND VESSELS

BACKGROUND

1. Technical Field

The present disclosure relates to in vivo systems and methods of identifying tissue parameters (e.g., tissue type) and assessing the conditions of the tissue during a surgical procedure. More specifically, the present disclosure relates to systems and methods for measuring the relative level of blood circulation in tissue with an energy-based surgical instrument for vessel sealing.

2. Background of Related Art

Correctly identifying tissue parameters including tissue type is important for any surgical operation. But it is especially important during laparoscopic operations when a surgeon can only view tissue through a camera. A camera, however, may provide a surgeon with a limited view of the tissue. As a result, several ex vivo and in vivo methods have been proposed to measure different characteristics of tissue in order to identify and assess the tissue.

Publication number US 2008/0200843 describes a method and apparatus for measuring human tissue properties in vivo. The method is based on sensing the mechanical response of tissue. The method includes applying a predetermined force to the surface of a patient with a probe and measuring the displacement of the probe as a function of applied force. Tissue properties are then determined based on the result of measuring the displacement of the probe.

Publication number US 2008/0154145 describes a method and apparatus for determining characteristics of biological tissues. Tissue characteristics are determined by introducing a sound wave into the tissue and recording the response of the tissue to the sound wave.

Publication number US 2009/0124902 describes a method for classifying tissue from the lumbar region using a combination of ultrasonic and optical measurements.

In publication number US 2007/0276286, a miniature electrode array is used to stimulate tissue and to measure a tissue response in order to provide tissue diagnosis and spatial tissue mapping.

Publication number US 2005/0283091 describes a method and apparatus for determining the conditions of biological tissue. The method includes exciting tissue with electrical signals at different frequencies and analyzing the cross-correlation of response signals with delayed excitation signals. Cross-correlation products are then auto-correlated. Cross-correlation products correspond to tissue conditions and auto-correlation products correspond to changes in the tissue conditions.

Publication number US 2003/0060696 discloses an apparatus for recognizing tissue type using multiple measurement techniques. For example, electrical signals are applied to a tissue via electrodes to measure impedance magnitude and phase at a plurality of frequencies. The phase information at the plurality of frequencies is compared with the phase information of known tissue types to identify the tissue type.

Publication number US 2002/0077627 describes a method for detecting and treating tumors using localized impedance measurements. The method includes providing an impedance measurement apparatus having a plurality of resilient members deployable to sample tissue impedance through a plurality of conductive pathways. Information from the impedance measurements is then used to determine the condition of the tissue.

Publication number US 2009/0253193 describes a device for characterizing tissue ex vivo. The device includes a set of independent electrodes that scan the tissue by moving a voltage gradient across the tissue surface and acquiring impedance spectrographs that may be mapped to an image.

U.S. Pat. No. 5,769,791 describes a tool for nondestructive interrogation of the tissue including a light source emitter and detector, which may be mounted directly on the surgical tool in a tissue contacting surface or mounted remotely and guided to the surgical field with fiber optic cables.

Publication number US 2009/0054908 describes a system having a surgical instrument with a sensor for generating a signal indicative of a property of a patient's tissue. The signal is converted into a current dataset and stored. A processor compares the current dataset with other previously stored datasets and uses the comparison to assess a physical condition of the tissue and/or to guide a procedure being performed on the tissue.

Although existing methods can provide various measurements of tissue parameters, these methods may be difficult to implement because of their complexity and may provide inaccurate measurements.

SUMMARY

The systems and methods according to embodiments of the present disclosure provide accurate information about tissue parameters and conditions. These systems and methods also provide a relatively quick and simple way to identify tissue parameters and conditions during laparoscopic procedures without requiring the introduction of additional instruments or tools into a patient's body.

According to one aspect, the present disclosure features a method of determining a tissue parameter. The method includes applying a probing signal to tissue, monitoring a response signal over an interval longer than an interval between two successive cardiac contractions, determining the amplitude of the response signal, determining the level of blood circulation in the tissue based upon the amplitude of the response signal, and determining a tissue parameter based upon the level of blood circulation. The probing signal is configured to interact with the tissue in a predetermined way.

In some embodiments, the tissue parameter is a tissue type, such as connective tissue, muscle tissue, nervous tissue, or epithelial tissue. In other embodiments, the tissue type includes a vessel type, such as a bile vessel, a lymph vessel, a blood vessel, an artery, an arteriole, a capillary, a venule, or a vein. In yet other embodiments, the tissue parameter is the tissue condition, such as whether the tissue is damaged.

In some embodiments, determining the amplitude of the response signal includes determining the amplitude of the response signal at the frequency of the cardiac contractions or at the harmonics of the frequency of the cardiac contractions. In other embodiments, the method of identifying tissue parameters may include applying the probing signal to different portions of the tissue, determining the amplitude of the resulting response signals to determine the level of blood circulation in the different portions of the tissue, and determining the tissue parameter based on the level of blood circulation in the different portions of the tissue.

The probing signal may be an acoustical signal, an optical signal, or an RF signal. In the case where the probing signal is an RF signal, monitoring the response signal includes monitoring the response signal at a frequency within a range from 10 kHz to 10 MHz. In some embodiments, monitoring the response signal includes monitoring the response signal with an energy-based tissue sealing instrument. In other embodiments, determining the amplitude of the response signal includes determining the amplitude and phase of the response signal.

In another aspect, the present disclosure features another method of determining a tissue parameter. The method includes applying a probing signal to tissue, monitoring a response signal that has interacted with the tissue over an interval longer than an interval between two successive cardiac contractions, monitoring a cardiac signal related to cardiac contractions, correlating the response signal and the cardiac signal, determining a level of blood circulation in the tissue based upon the result of correlating the response signal and the cardiac signal, and determining a parameter of the tissue based upon the result of determining the level of blood circulation in the tissue. In some embodiments, the parameter of the tissue is a type of the tissue. The type of the tissue may be connective tissue, muscle tissue, nervous tissue, or epithelial tissue.

In yet another aspect, the present disclosure features a system for determining a tissue parameter. The system includes a probing signal source configured to apply a probing signal to tissue, a response signal monitor configured to monitor a response signal over an interval longer than an interval between two successive cardiac contractions, and a processor configured to analyze the amplitude of the response signal to determine a level of blood circulation in the tissue. The processor is further configured to determine a tissue parameter based on the level of blood circulation. In some embodiments, the system further includes an electrosurgical energy source configured to apply electrosurgical energy to tissue during an electrosurgical procedure. In these embodiments, the probing signal source is the same source as the electrosurgical energy source.

BRIEF DESCRIPTION OF THE DRAWINGS

The systems and methods of in vivo assessment of tissues and vessels will now be described with reference to the accompanying drawings, in which.

DETAILED DESCRIPTION

Different types of human and animal tissues have different densities of blood vessels (i.e., the number of blood vessels per unit area or volume of tissue) and experience different levels of blood circulation (i.e., the amount of blood flow per unit volume of tissue). These parameters can be used to identify different types of tissues during a surgical procedure. For example, when the tissue structure changes as a result of damage to the tissue, the blood circulation usually changes as well. This phenomenon allows one to distinguish between damaged and normal portions of tissue by comparing corresponding levels of blood circulation. As another example, when tumors form and grow in normal tissue, the density of blood vessels in the tissue increases because these tumors depend on the formation of new blood vessels for their growth. Thus, by measuring the density of blood vessels or the level of blood circulation in tissue, one can distinguish between a tumor and normal tissue.

For some surgical procedures, such as electrosurgical procedures, the surgeon may need to distinguish between blood vessels and other types of vessels, e.g., bile ducts. For blood vessels, the surgeon may need to check for blood clots or other structural changes in the blood vessels. For vessel sealing procedures, the surgeon may need to confirm that the vessel has been properly sealed before it is cut. In all of these procedures, the tissue or vessel can be examined to assess blood circulation conditions. Information regarding blood circulation conditions may inform a surgeon regarding the type of the tissue or vessel and/or the condition of the tissue or vessel.

Figure 1:
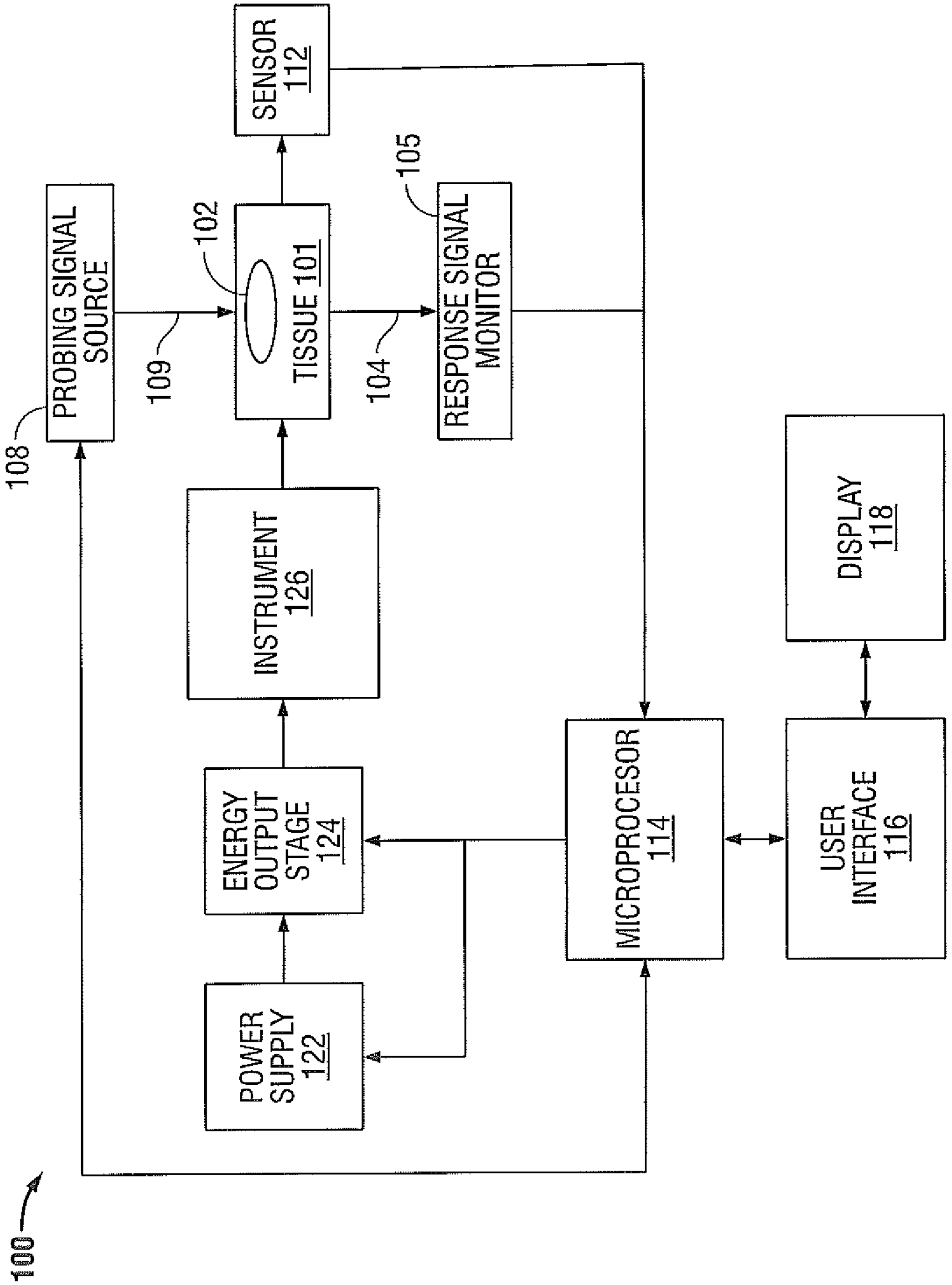
FIG. 1 is a block diagram of a system for recognizing tissue and vessels based on blood circulation according to embodiments of the present disclosure.

FIG. 1 is a block diagram of an energy-based tissue-sealing system 100 for recognizing tissue or vessels based upon blood circulation in the tissue or vessels according to embodiments of the present disclosure. The system 100 (and the methods described below) may use any type of energy to seal tissue including mechanical energy, acoustical energy, thermal energy, electric energy, or electromagnetic energy (e.g., optical energy or radio frequency (RF) energy).

The system 100 includes a power supply 122, an energy output stage 124, and an instrument 126. The power supply 122 supplies power to the energy output stage 124, which generates energy and provides the energy to the instrument 126. The instrument 126, in turn, applies the generated energy to the tissue 101, which includes at least one vessel 102. For an RF-based tissue-sealing system, the energy output stage 124 generates RF energy and the instrument 126 applies the RF energy to the tissue 101 through at least one contact to seal the tissue 101.

The system 100 also includes a sensor 112, a microprocessor 114, a user interface 116, and a display 118. The sensor 112 senses various parameters and/or properties of tissue 101 at the operating site and transmits sensor signals representing the sensed parameters or properties of the tissue 101 to the microprocessor 114. The microprocessor 114 processes the sensor signals and generates control signals based on the processed sensor signals to control the power supply 122 and/or the energy output stage 124. For example, the microprocessor 114 may regulate the voltage or current output from the power supply 122 or the energy output stage 124 based on the processed sensor signals.

The sensor 112 is configured to measure various electrical or electromechanical conditions at the operating site such as tissue impedance, changes in tissue impedance, tissue temperature, changes in tissue temperature, leakage current, applied voltage, and applied current. The sensor 112 continuously measures one or more of these conditions so that the microprocessor 114 can continually adjust the energy output from the power supply 122 and/or the energy output stage 124 during a sealing procedure. For example, in an RF-based vessel sealing instrument, the sensor 112 may measure tissue impedance and the microprocessor 114 may adjust the voltage generated by the energy output stage 124.

The user interface 116 is coupled to the microprocessor 114 allowing a user to control various parameters of the energy applied to the tissue 101 during a surgical procedure. For example, the user interface 116 may allow a user to manually set, regulate and/or control one or more parameters of the energy delivered to the tissue, such as voltage, current, power, frequency, and/or pulse parameters, e.g., pulse width, duty cycle, crest factor, and/or repetition rate.

The microprocessor 114 can execute software instructions for processing data received from the user interface 116 and for outputting control signals to the power supply 122 and/or the energy output stage 124. The software instructions are stored in an internal memory of the microprocessor 114, an internal or external memory bank accessible by the microprocessor 114 and/or an external memory, e.g., an external hard drive, floppy diskette, or CD-ROM. Control signals generated by the microprocessor 114 may be converted to analog signals by a digital-to-analog converter (DAC) (not shown) before being applied to the power supply 122 and/or energy output stage 124.

For some embodiments of an RF-based tissue-sealing system, the power supply 122 is a high-voltage DC power supply that produces RF current. In these embodiments, the microprocessor 114 transmits control signals to the power supply to control the magnitudes of the RF voltage and current output from the power supply 122. The energy output stage 124 receives the RF current and generates one or more pulses of RF energy. The microprocessor 114 generates control signals to regulate the pulse parameters of the RF energy, such as pulse width, duty cycle, crest factor, and repetition rate. In other embodiments, the power supply 122 is an AC power supply, and the energy output stage 124 may vary the waveform of the AC signal generated by the power supply 122 to achieve a desired waveform.

As described above, the energy-based tissue-sealing system 100 includes a user interface 116. The user interface 116 includes an input device, such as a keyboard or touch screen, through which a user enters data and commands. The data may include the type of instrument, the type of procedure, and/or the type of tissue. The commands may include target effective voltage, current, or power level, or other commands for controlling parameters of the energy that is delivered from the energy output stage 124 to the instrument 126.

The system 100 also includes a probing signal source 108 and a response signal monitor 105. The probing signal source 108 applies a probing signal 109 to the tissue 101 and the response signal monitor 105 senses a response signal 104. The response signal 104 is the probing signal 109 that has been transmitted and/or scattered by the tissue 101 and vessel 102. The probing signal 109 and the response signal 104 may be acoustical signals, optical signals, RF signals, or any combination of these signals. In some embodiments, the probing signal source 108 is the energy output stage 124. The energy output stage 124 may generate a probing signal 109 that is the same as the electrosurgical energy applied to the tissue 101 to perform an electrosurgical procedure (e.g., vessel sealing). Alternatively, the energy output stage 124 may generate a probing signal 109 that has parameters that are different from the parameters of the electrosurgical energy applied to the tissue 101.

The response signal monitor 105 generates a sensor signal or sensor data based on the response signal 104 and transmits the sensor signal or sensor data to the microprocessor 114. The microprocessor 114 processes the sensor signal or sensor data to determine the level of blood circulation in the tissue 101 or vessel 102. For example, the microprocessor 114 may determine the level of blood circulation based on the magnitude of the sensor signal or the response signal 104.

The response signal 104 may provide information about the tissue type. For example, the response signal 104 may identify the tissue as connective tissue, muscle tissue, nervous tissue, epithelial tissue, or any combination of these tissue types. The response signal 104 may also identify the vessel type within the tissue 101. The vessel types include bile vessels, lymph vessels, and blood vessels. The response signal 104 may distinguish the type of blood vessel that resides in a given portion of tissue. The types of blood vessels include arteries, arterioles, capillaries, venules, and veins. The response signal 104 may also be used to identify the condition of the tissue, such as whether the tissue is damaged.

The system 100 may determine the level of blood circulation by sensing tissue parameters or properties that depend on the level of blood circulation during a period exceeding one cardiac cycle. In some embodiments, the system 100 may sample tissue parameters or properties for multiple cardiac cycles to more accurately determine the level of blood circulation. In other embodiments, a cardiac signal, which is related to heart contractions (e.g., an electrocardiographic signal), can be used to evaluate the correlation between the parameters of the sensor signal and the cardiac signal to more accurately assess the level of blood circulation.

Figure 2A:
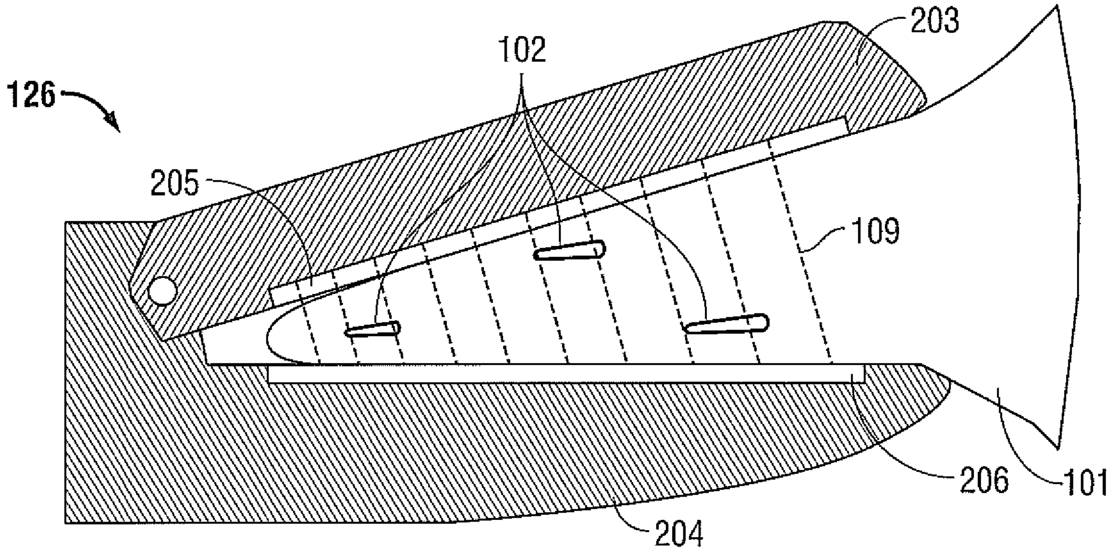
FIGS. 2A and 2B are cross-sectional side views of a portion of the instrument of FIG. 1 having jaw members for grasping tissue and blood vessels according to embodiments of the present disclosure.
Figure 2B:
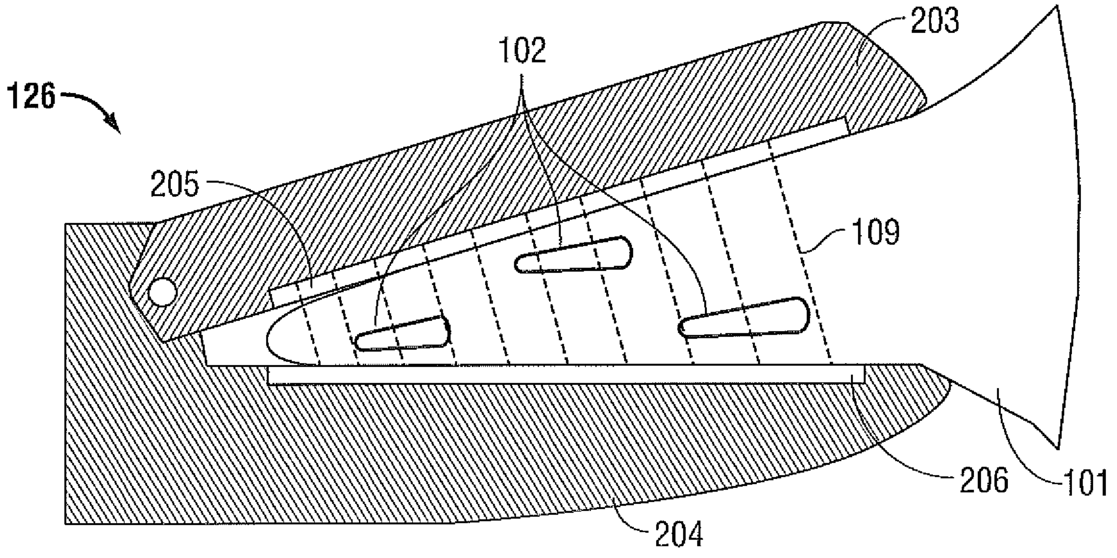

FIGS. 2A and 2B show portions of an embodiment of the energy-based instrument 126 of FIG. 1 having jaw members 203, 204 configured to grasp and compress tissue 101 and vessels 102. The jaw members 203, 204 include electrodes or contacts 205, 206 that are electrically coupled to the energy output stage 124. The electrodes 205, 206 receive energy from the energy output stage 124 and apply it to the tissue 101 and vessels 102 to seal the tissue 101 and vessels 102.

As described above, the energy-based instrument 126 is also configured to evaluate blood circulation in a given volume of tissue 101. To evaluate blood circulation, the given volume of tissue 101 is first grasped between the jaw members 203, 204 of the energy-based instrument 126. The pressure that is applied to the tissue 101 by the jaw members 203, 204 is selected to provide electrical contact between the electrodes 205, 206 and the tissue 101. However, the amount of pressure applied to the tissue 101 may be lower than the amount of pressure used to compress the tissue 101 during tissue sealing. Then, a probing signal 109 (e.g., an RF signal) is applied to the tissue 101 by the electrodes 205, 206 and a response signal 104 (e.g., tissue impedance) is measured during one or more cardiac cycles.

During the cardiac cycles, the pressure of the blood flowing in the blood vessels 102 varies and, as a result, the relative amount of blood in a given volume of tissue 101 also varies. For example, as shown in FIG. 2A, during a first portion of the cardiac cycle, the pressure of the blood flowing within the blood vessels 102 is at a low level and the volume of blood within the given volume of tissue 101 is at a low level. On the other hand, as shown in FIG. 1B, during a second portion of the cardiac cycle, the pressure of the blood flowing within the blood vessels 102 is at a high level and the volume of blood within the given volume of tissue 101 is at a high level. The volume of blood within the given volume of tissue 101 may be measured by measuring the impedance of the tissue 101. The impedance may be measured by applying the probing signal 109 to the tissue 101 and sensing the response signal 104.

During a cardiac cycle, as the volume of blood in a given volume of tissue increases, a force is applied to the jaw members 203, 204 to increase the distance between the jaw members 203, 204. In some embodiments, the system 100 includes a motion sensor configured to sense the change in distance between the jaw members 203, 204. This distance information may be used together with the response signal 104 to evaluate the level of blood circulation within a given volume of tissue 101.

As described above, a probing signal 109 is applied to a vessel and a response signal 104 is measured over time to identify tissue 101 and/or vessels 102 or to determine parameters of the tissue 101 and/or the vessels 102. The response signal 104 may include the frequency and amplitude of an electrical impedance of the tissue 101. If the frequency of the electrical impedance correlates to the frequency of cardiac contractions, then the vessel 102 is identified as a blood vessel. If the vessel is identified as a blood vessel, the amplitude of the electrical impedance would indicate the level of blood circulation.

Figure 3:
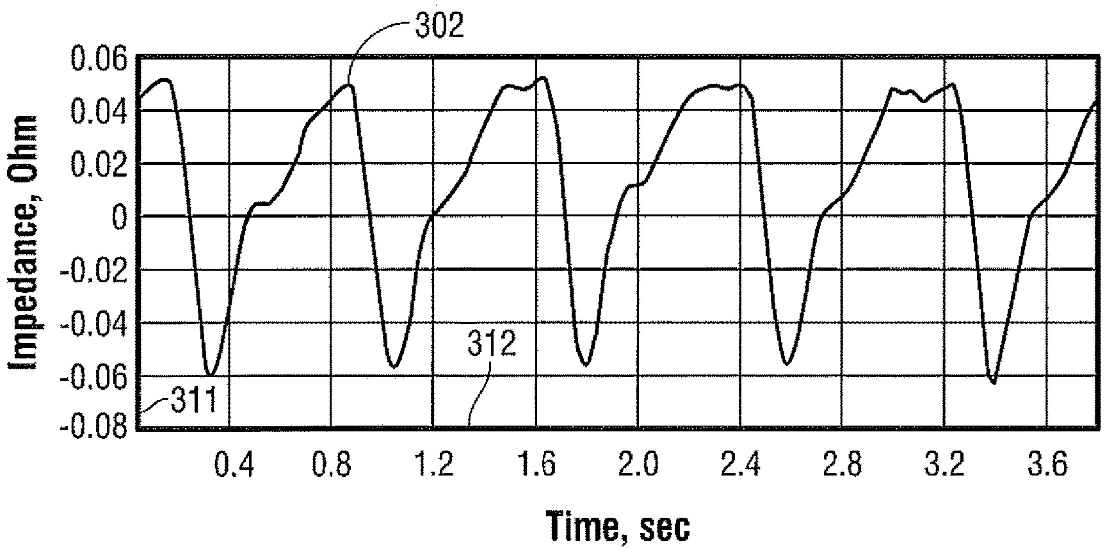
FIG. 3 is a graphical diagram showing impedance variations induced by blood circulation and measured with an RF-based tissue sealing device according to embodiments of the present disclosure.

FIG. 3 is a graph showing experimentally-measured impedance of tissue 302 versus time. The graph has a y-axis 311 that indicates the tissue impedance in ohms and an x-axis 312 that indicates the time in seconds. As shown in FIG. 3, the measured impedance 302 continually varies according to the cardiac cycles where a cardiac cycle is the distance between the peaks of the measured impedance 302. In this case, the measured impedance 302 has a peak-to-peak amplitude of approximately 0.1 ohms and a period of approximately 0.8 seconds (which corresponds to a heart rate of 75 beats per minute). The measured impedance 302 varies according to the cardiac cycles because the volume of blood within a given volume of tissue 101 varies according to the cardiac cycles. In other words, the measured impedance 302 correlates with the volume of blood within a given volume of tissue 101. Depending on the design of the instrument, it is also possible that an increase in blood pressure can expand the grasped tissue and, as a result, the tissue volume between the jaw members changes. This effect may also contribute to variations in measured impedance.

Figure 4:
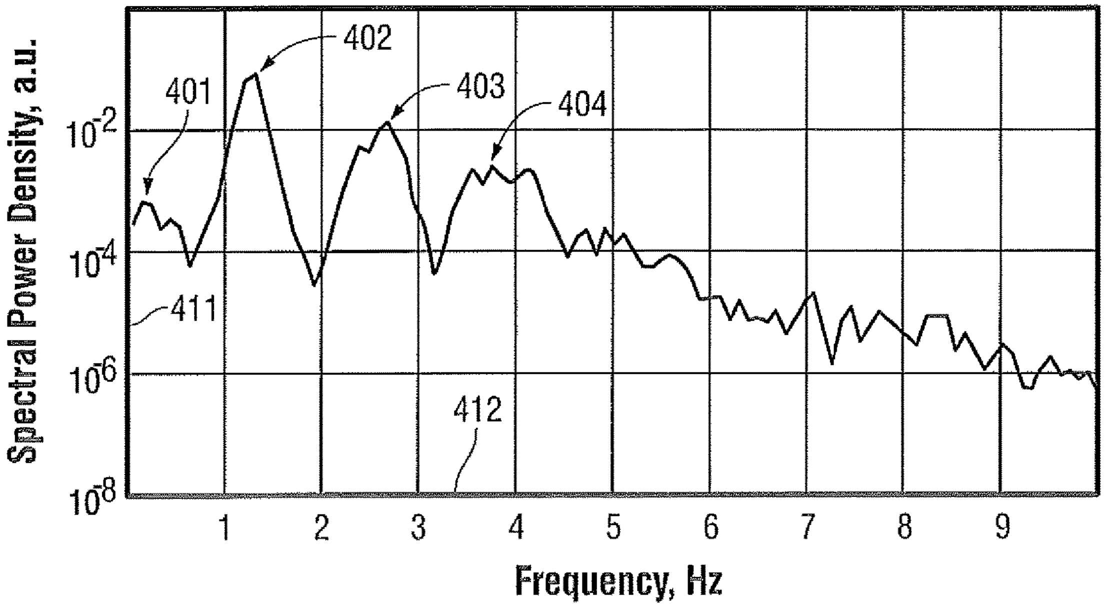
FIG. 4 is a graphical diagram showing the frequency spectrum of the impedance variations illustrated in FIG. 3.

FIG. 4 is a graph showing the frequency spectrum of experimentally-measured impedance variations in tissue corresponding to FIG. 3. The graph has a y-axis 411 that indicates the spectral power density of the experimentally-measured impedance variations in tissue and an x-axis 412 that indicates the frequency in Hertz. The graph shows modulation variations related to the fundamental frequency of cardiac contractions 402 and its harmonics 403, 404. In this case, the fundamental frequency of cardiac contractions 402 is approximately 1.25 Hz, which corresponds to a cardiac cycle of approximately 0.8 seconds in FIG. 3. The measured impedance also includes variations related to breathing 401 and the inter-modulation products between the variations due to heart contraction and the variations due to breathing.

Figure 5:
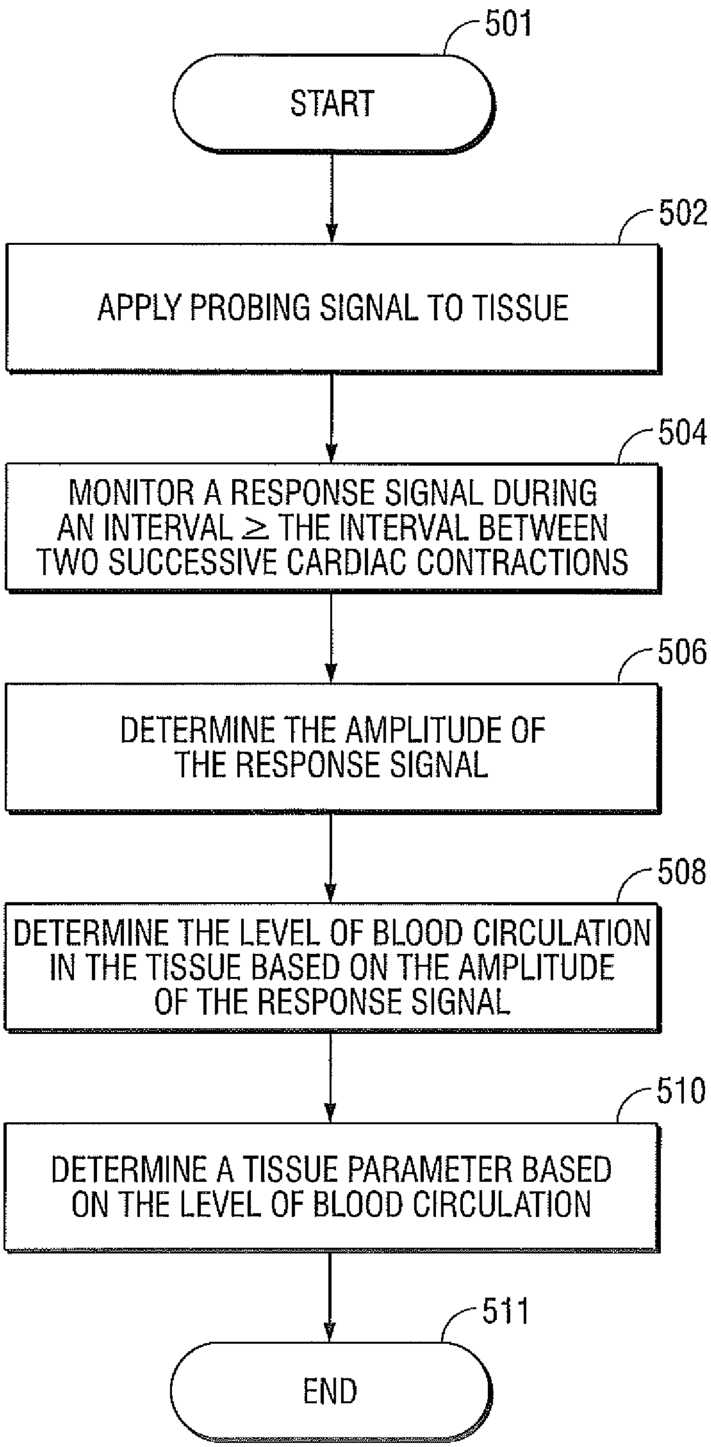
FIGS. 5 and 6 are flow diagrams of methods for recognizing parameters of tissue and vessels according to embodiments of the present disclosure.

FIG. 5 is a flow diagram of a process for identifying parameters of tissue and vessels according to embodiments of the present disclosure. After the process starts in step 501, a probing signal 109 is applied to tissue in step 502. The probing signal 109 interacts with the tissue to create a response signal 104. In step 504, the response signal 104 is monitored over an interval equal to or longer than an interval between two successive cardiac contractions. The response signal may be monitored at a frequency within a range between 10 kHz and 10 MHz using, e.g., an energy-based tissue sealing instrument.

Next, in step 506, the amplitude of the response signal 104 is determined. The amplitude of the response signal 104 may be determined at a frequency of the cardiac contractions or at the harmonics of the frequency of the cardiac contractions. Then, in step 508, the level of blood circulation in the tissue is determined based on the amplitude of the response signal 104. In other embodiments, the amplitude and phase of the response signal 104 are analyzed to determine the level of blood circulation in the tissue. Finally, before the process ends in step 511, a tissue parameter is determined in step 510 based on the level of blood circulation.

In some embodiments, the probing signal source 108 of FIG. 1 applies a probing signal to different portions of the tissue. The response signal monitor 105 then monitors parameters of the response signals and the microprocessor 114 determines the level of blood circulation in different portions of the tissue based on the response signals. The microprocessor 114 may also determine parameters of the tissue based on the level of blood circulation in different portions of the tissue.

Figure 6:
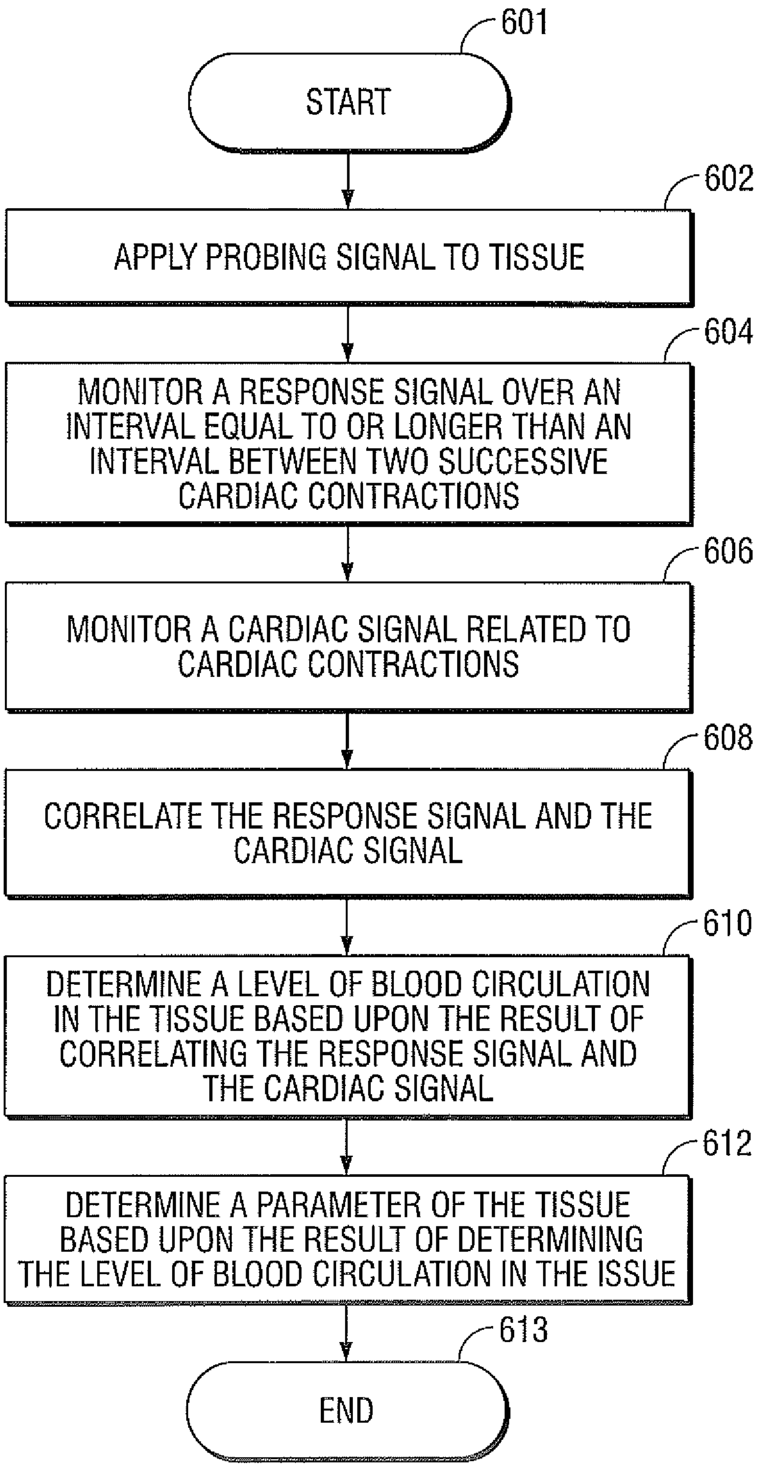

FIG. 6 is a flow diagram of a process for identifying parameters of tissues and vessels according to other embodiments of the present disclosure. As in FIG. 5, after the process starts in step 601, a probing signal 109 is applied to tissue in step 602. The probing signal 109 interacts with the tissue to create a response signal 104. In step 604, the response signal 104 is monitored over an interval equal to or longer than an interval between two successive cardiac contractions. In addition, a cardiac signal related to cardiac contractions is monitored in step 606. In step 608, the response signal 104 and the cardiac signal are correlated. Then, in step 610, the level of blood circulation in the tissue is determined based upon the result of correlating the response signal 104 and the cardiac signal. Finally, before the process ends in step 613, a tissue parameter is determined in step 612 based upon the result of determining the level of blood circulation in the tissue. As described above, the tissue parameter may include the tissue type, such as connective tissue, muscle tissue, nervous tissue, or epithelial tissue.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

The invention claimed is:

1. A method of determining a tissue parameter for an energy-based tissue-sealing system, comprising:

grasping tissue using two jaw members;

applying a probing signal to the tissue, the probing signal being configured to interact with the tissue;

over an interval longer than an interval between two successive cardiac contractions, monitoring a response signal in response to the probe signal and changes in distance between the two jaw members caused by the cardiac contractions;

processing, using a processor, the monitored cardiac contractions, the changes in distance, and the response signal to determine a tissue parameter by:

determining amplitudes of the response signal in the tissue over the interval longer than the interval between two successive cardiac contractions;

determining levels of blood circulation in the tissue based upon the amplitudes of the response signal and the changes in distance between the two jaw members over the interval longer than the interval between two successive cardiac contractions; and determining a tissue parameter based upon the levels of blood circulation; and adjusting energy output from an energy output stage of the energy-based tissue-sealing system based on the tissue parameter.

2. The method of claim 1, wherein the tissue parameter is a tissue type.

3. The method of claim 2, wherein the tissue type is selected from the group consisting of connective tissue, muscle tissue, nervous tissue, and epithelial tissue.

4. The method of claim 2, wherein the tissue type includes a vessel type.

5. The method of claim 4, wherein the vessel type is selected from the group consisting of an artery, an arteriole, a capillary, a venule, and a vein.

6. The method of claim 1, wherein the tissue parameter is a tissue condition.

7. The method of claim 6, wherein the tissue condition is whether the tissue is damaged.

8. The method of claim 1, wherein applying the probing signal to tissue includes applying the probing signal to different portions of the tissue, wherein determining the amplitudes of the response signal includes determining the amplitudes of each response signal at the frequencies of cardiac contractions to determine the levels of blood circulation in each different portion of the tissue, and wherein determining the tissue parameter includes determining the tissue parameter based on the levels of blood circulation in each different portion of the tissue.

9. The method of claim 1, wherein the probing signal is selected from the group consisting of an acoustical signal, an optical signal, and an RF signal.

10. The method of claim 1, wherein the probing signal is an RF signal, and wherein monitoring the response signal includes monitoring the response signal at a sampling frequency within a range from 10 kHz to 10 MHz.

11. The method of claim 1, wherein monitoring the response signal includes monitoring the response signal with an energy-based tissue sealing instrument.

12. The method of claim 1, wherein determining the amplitudes of the response signal includes determining a phase of the response signal.

13. The method of claim 1, wherein the response signal is the probe signal that has been scattered or transmitted by the tissue.

* * * * *